US008680024B2

(12) United States Patent
Coyer et al.

(10) Patent No.: US 8,680,024 B2
(45) Date of Patent: *Mar. 25, 2014

(54) METHODS FOR SCREENING AND ARRAYING MICRORGANISMS SUCH AS VIRUSES USING SUBTRACTIVE CONTACT PRINTING BACKGROUND

(75) Inventors: Sean R. Coyer, Atlanta, GA (US); Emmanuel Delamarche, Rueschlikon (CH); Daniel J. Solis, San Diego, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/429,929

(22) Filed: Mar. 26, 2012

(65) Prior Publication Data

US 2012/0184458 A1   Jul. 19, 2012

Related U.S. Application Data

(63) Continuation of application No. 12/195,577, filed on Aug. 21, 2008.

(51) Int. Cl.
*C40B 50/18* (2006.01)

(52) U.S. Cl.
USPC .......................................................... 506/32

(58) Field of Classification Search
None
See application file for complete search history.

(56) References Cited

U.S. PATENT DOCUMENTS

2007/0129321 A1   6/2007   Mirkin et al.

FOREIGN PATENT DOCUMENTS

| EP | 1691196 A | 8/2006 |
|---|---|---|
| WO | 0244733 A2 | 6/2002 |
| WO | 2004056470 A1 | 7/2004 |
| WO | 2005012872 A2 | 2/2005 |
| WO | 2006055925 A2 | 5/2006 |
| WO | 2007082057 A2 | 7/2007 |
| WO | 2008020851 A2 | 2/2008 |

OTHER PUBLICATIONS

Whaley, Sandra R. et al., "Selection of peptides with semiconductor binding specificity for directed nanocrystal assembly", letters to nature, vol. 408, Jun. 8, 2000, www.nature.com (c) 2000 Macmillan Magazines Ld., pp. 665-668.
Bernard, Andre et al., "Microcontact Printing of Proteins", Advanced Materials, Jul. 19, 2000, vol. 12, No. 14, p. 1067-1070.
Chang-Yen, David A. et al. "A Novel PDMS Microfluidic Spotter for Fabrication of Protein Chips and Microarrays", Journal of Microelectromecahnical Systems, vol. 15, No. 5, Oct. 2006, pp. 1145-1151.

(Continued)

*Primary Examiner* — Christian Boesen
(74) *Attorney, Agent, or Firm* — Cantor Colburn LLP; Daniel Morris

(57) ABSTRACT

Methods for screening and arranging microorganisms such as viruses in an array using subtractive contact printing are provided. In one embodiment, a method for forming an array of receptors for microorganisms comprises: patterning an array of structures on a first substrate to form a template on a surface of the first substrate; applying a receptor material to a face of a second substrate; and contacting the face of the second substrate with the template to remove a portion of the receptor material from the second substrate, thereby forming an array of receptors on the second substrate.

11 Claims, 3 Drawing Sheets

(56) References Cited

OTHER PUBLICATIONS

Cheung, Chin Li, et al., Fabrication of Assembled Virus Nanostructures on Templates of Chemoselective Linkers Formed by Scanning Probe Nanolithography, JACS Communications, Feb. 3, 2003, p. 125, p. 6848-6849, Chemical and Materials Science Directorate, La Jolla, California.

Coyer, Sean R., et al. Abstract of Facile Preparation of Complex Protein Architures with Sub-100-nm Resolution on Surfaces—A Journal fo the Gesellschaft Deutscher Chemiker Angewandte Chemie 2007-46/36 published on line Sep. 4, 2007 at 4:10 a.m.

Coyer, Sean R., et al., Facile Preparation of Complex Protein Architectures with Sub-100-nm Resolution on Surfaces, Nanolithography, 2007, p. 1-5, Wiley-VCH Verlag GmbH & Co. KGaA, Weinheim.

Coyer, Sean R., et al. Facile Preparation of Complex Protein Architecutres with Sub-100-nm Resolution on Surfaces, Angewandte Chemie, Nanolithography, Angew. Chem. Int. Ed. 2007, vol. 46, pp. 6837-6840 (c) Wiley-VCH Verlag GmbH & Co. KGaA, Weinheim.

Coyer, Sean R., et al., "Facile Preparation of Complex Protein Architectures with Sub-100-nm Resolution on Surfaces" (Jun. 19, 2007) Angewandte Chemie International Edition 2007, vol. 46, pp. 6837-6840 (downloaded Jan. 31, 2010) from http://www3.interscience.wiley.com/journal/114280769/abstract?CRETRY=1&SRETRY=0) web article site from pubmed link.

Abstract of Wiley InterScience—Journals—Angewandte Chemie—International Edition—Table of Contents, vol. 46, Issue 36, pp. 6741-6931, physically published Sep. 10, 2007.

Gervais, L., et al. "Immobilization of biotinylated bacteriophages on biosensor surfaces", available online at www.sciencedirect.com, Sensors and Actuators B125 (2007) pp. 615-621.

International Search Report mailed Nov. 5, 2009 for PCT/IB2009/053098, 4 pgs.

Solis, Daniel J., et al. "Large-Scale Arrays of Aligned Single Viruses", XP-002550940; Advanced Materials, 2009, 21, pp. 1-4.

Stamou, Dimitrios, et al., Self-Assembled Microarrays of Attoliter Molecular Vessels, Angewandte Chemie International Edition a Journal of the Gesellschaft Deutscher Chemicker, Nov. 24, 2003, p. 5580-5583, Wiley-Vch.

Suh, Kahp Y., et al., Direct Confinement of Individual Viruses within Polyethylene Glycol (PEG) Nanowells, Nano Letters, 2006, p. 1196-1201, vol. 6, No. 6, American Chemical Society, Cambridge, Massachusetts.

Vega, Rafael A., et al., Nanoarrays of Single Virus Particles, Angewandte Chemie International Edition a Journal of the Gesellschaft Deutscher Chemiker, 2005, p. 6013-6015, Wiley-Vch.

Advisory Action issued in U.S. Appl. No. 13/429,929 dated Mar. 28, 2013; 3 pages.

Amendment to Office Action Filed in U.S. Appl. No. 12/195,577 dated Mar. 19, 2013; 12 pages.

Request for Continued Examination Filed in U.S. Appl. No. 12/195,577 dated Apr. 17, 2013; 3 pages.

Coyer, Sean R. et al., "Facile Preparation of Complex Protein Architectures with Sub-100-nm Resolution on Surfaces", Angew. Chem. Int. Ed., 2007, vol. 46, No. 36, pp. 6837-6840.

Tatsuyuki, Nakatani., "English Abstract for Cell Array Sorter, Method for Producing the Same and Method for Sorrting Cell by Using the Same". Japanese Application No. JP2007-202489 A, published on Aug. 16, 2007; 2 pages.

Final Office Action issued in U.S. Appl. No. 12/195,577, mailed Jan. 24, 2013; 16 pages.

Non Final Office Action issued in U.S. Appl. No. 12/195,577 dated May 22, 2013; 14 pages.

METHODS FOR SCREENING AND ARRAYING MICRORGANISMS SUCH AS VIRUSES USING SUBTRACTIVE CONTACT PRINTING BACKGROUND

CROSS-REFERENCE TO RELATED APPLICATION

This application is a DIVISIONAL CONTINUATION of U.S. patent application Ser. No. 12/195,577, filed Aug. 21, 2008, the disclosure of which is also incorporated herein by reference in its entirety.

FIELD OF THE INVENTION

This invention relates to biological library screening, and particularly to methods for screening and arranging viruses in an array using subtractive contact printing.

DESCRIPTION OF BACKGROUND

Substantial attention has been directed to synthesizing interesting molecules such as peptides, drugs, enzymes, catalysts, functional organic materials and ligands for biological receptors by preparing large random biological libraries. Such libraries are often based on using microorganisms. Each microorganism synthesizes one type of molecule, and a large chemical diversity is achieved by employing libraries containing a large number of microorganisms. The most used microorganisms for preparing libraries are yeast and bacteriophages. In the particular case of bacteriophages, also called phages, the molecule of interest can be displayed at the surface of the phage. Inside the phage resides the oligonucleotide sequence (the gene) that encodes for the displayed protein. This makes bacteriophages a very convenient tool for preparing and screening libraries because when an interaction is found between the molecule of interest and a target, the structure of the molecule can be deciphered by sequencing the gene encoding it. Unfortunately, screening a particular molecule of interest in the library can be very difficult. For example, one method currently employed to screen for a particular type of phage entails adding a phage library to a microtiter plate well that is coated with a receptor capable of attaching to a particular type of phage. After allowing a portion of the phages to bind to the receptor, either specifically or non-specifically, the unbound phages can be removed through washing. The bound receptors can then be recovered and copied to increase their numbers. The foregoing selection method can be repeated until genetic sequences show consensus. Several screening rounds can be required since a library can contain billions of different phages, each expressing a unique library element.

Biologically inspired approaches have been developed for improving the screening of viruses in a library. These approaches provide for the self-assembly or directed assembly of viruses such as baferiophages (i.e., viruses that infect bacteria) in an array using chemical linkers, nucleic acid hybridization, or metal ions. The filamentous M13 bacteriophage virus, in particular, has shown a tremendous capacity for incorporating biological and inorganic materials (including metallic, magnetic, and semi-conducting) into its self-assembled, genetically-modifiable architecture. Macroscopic organization of M13 bacteriophages has been achieved using liquid crystalline phase separation phenomena and virus-membrane complexes, creating materials of high uniformity and element density.

Unfortunately, current self-assembly and directed assembly methods often face a trade off between specificity and generality of the approach. The use of highly specific antibody interactions, however, has remained relatively unexplored due to the gross loss of antibody activity during sample preparation and processing. Soft lithographic methods, including microcontact printing, have been successful in maintaining the biomolecular activities of antibodies but are limited in feature size and pitch due to the mechanical properties of the elastomeric materials used in the printing of the antibodies.

BRIEF SUMMARY

The shortcomings of the prior art are overcome and additional advantages are provided through the provision of methods for screening and arranging microorganisms such as viruses in an array using subtractive contact printing. In one embodiment, a method for forming an array of receptors for microorganisms comprises: patterning an array of structures on a first substrate to form a template on a surface of the first substrate; applying a receptor material to a face of a second substrate; and contacting the face of the second substrate with the template to remove a portion of the receptor material from the second substrate, thereby forming an array of receptors on the second substrate.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION

Turning now to the drawings in greater detail, it will be seen that FIGS. 1-5 illustrate an exemplary embodiment of a method for screening viruses such as bacteriophages using subtractive contact printing. This method can be used to pattern a densely packed array of nanoscale protein receptors capable of capturing certain viruses present in a library of viruses. The conditions for the binding of the viruses to the receptors can be controlled to prevent non-specific binding, to prevent aggregation and damage of the viruses, and to reduce the number of viruses binding to each protein receptor down to as low as one. As such, a large number of viruses can be screened from a very large library in a relatively short period of time.

Figure 1:
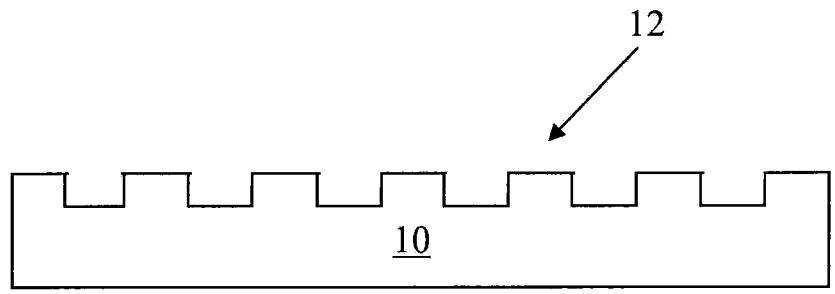
FIGS. 1-5 illustrate one example of a method in which subtractive contact printing is used to arrange viruses in an array to allow certain viruses to be screened.

As shown in FIG. 1, the screening method involves first patterning a substrate, e.g., a silicon-based substrate, to form a template 10 for subtractive contact printing comprising an array of structures 12. The structures 12 can be formed by using a lithography technique to pattern resist upon selected portions of the substrate and then using an etch technique, e.g., reactive ion etching, to remove portions of the substrate not protected by the patterned resist. In one embodiment, electron-beam lithography is used to achieve high-resolution patterning of the resist. The resulting template 10 can then be cleaned by, e.g., treating it with an oxygen-bearing plasma.

Figure 2:
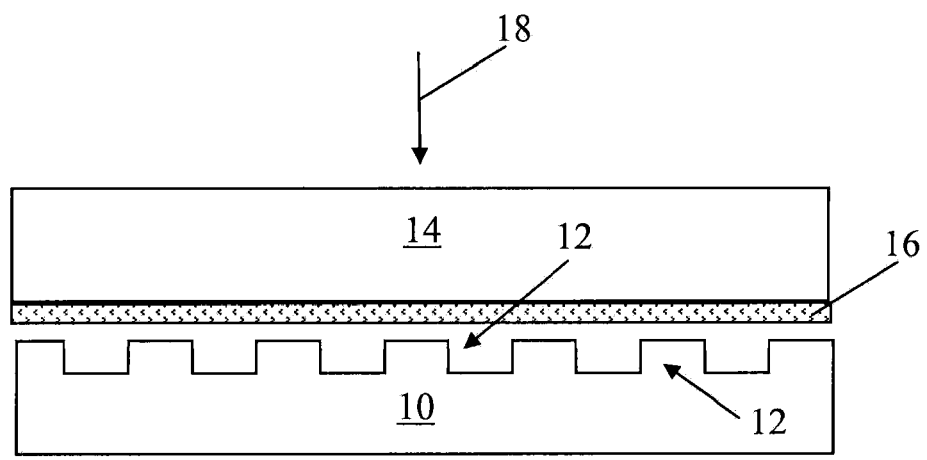

As shown in FIG. 2, the method described herein also involves obtaining a substrate having a substantially planar face for use as a stamp 14 and applying a receptor material 16 to the planar face of the stamp 14. The stamp 14 can comprise a material having a sufficient amount of mechanical deformability to follow the contours of surfaces with which it is placed in contact. Examples of suitable materials for use as stamp 14 include but are not limited to elastomers such as polydimethylsiloxane. Elastomers in general can be used for this purpose owing to their good mechanical deformability, which allows them to follow the contours of surfaces with which they are put in contact. Specific examples of elastomers are thermoplastic elastomers such as styrenic block copolymers, polyolefin-based elastomers, polyamides, polyurethanes, and copolyesters. Rubber-like elastomers such as polybutadiene, polyisoprene, polyisobutylene, and fluorinated silicone elastomers can also be used. The surface of the stamp 14 is ideally, but not necessarily, hydrophobic to allow proteins to be deposited from solution onto its surface. In this case, deposition of proteins is spontaneous and self-limiting, making the inking of the stamp 14 very simple to perform by simply covering its surface with proteins dissolved in a buffer solution. The stamp 14 can also be treated using an oxygen plasma or ultraviolet radiation and ozone to oxidize its surface. This oxidative treatment renders the surface of the stamp 14 more hydrophilic and can be used for depositing polar, charged, and/or hydrophilic receptor material on it.

Although this embodiment is described mostly with the example of using protein receptors, many other types of receptor materials can be used as well. Examples of suitable receptor materials include but are not limited to any protein, biomolecule, or chemical to which a microorganism, e.g., a virus, being screened is capable of binding. Specific examples of receptor materials are a protein, an antibody, an antibody fragment, a complex formed of multiple antibodies, an enzyme, a peptide, a cell adhesion molecule, a protein receptor, deoxyribonucleic acid (DNA), ribonucleic acid (RNA), a sugar, an oligonucleotide, and a complex formed of several oligonucleotides. The application of the receptor material 16 can be achieved by, for example, placing the stamp 14 face-up in a Petri dish and by covering it with a solution of the receptor material. During this step, i.e., the inking step, some of the receptors contained in the solution deposit on the stamp 14. The amount of receptor deposited on the stamp 14 depends on the affinity between the receptor material 16 and the stamp 14, the duration of the inking step, the concentration of the receptor material in the inking solution, the type of solution used, and how the stamp 14 is rinsed. When proteins receptors 16 are inked on the stamp 14, the concentration of receptor in the inking solution can be, for example, about 1 μg/mL (microgram/milliliter) to about 1 mg/mL (milligram/milliliter). Inking can be done overnight at 4° C. or at room temperature within 20 minutes. The amount of receptor material deposited for particular inking conditions can be indirectly determined by measuring the thickness and composition of a receptor material transferred (by printing) from the substrate 14 to a planar surface such as the native oxide of a silicon wafer. X-ray photoemission spectroscopy and ellipsometry can be used to characterize the amount of the printed receptor material. After inking and rinsing, the stamp 14 can be dried under a stream of nitrogen to prevent it from being covered by a liquid film. Such a film of liquid might otherwise interfere with the transfer of receptor material 16 to the array of structures 12.

Figure 3:
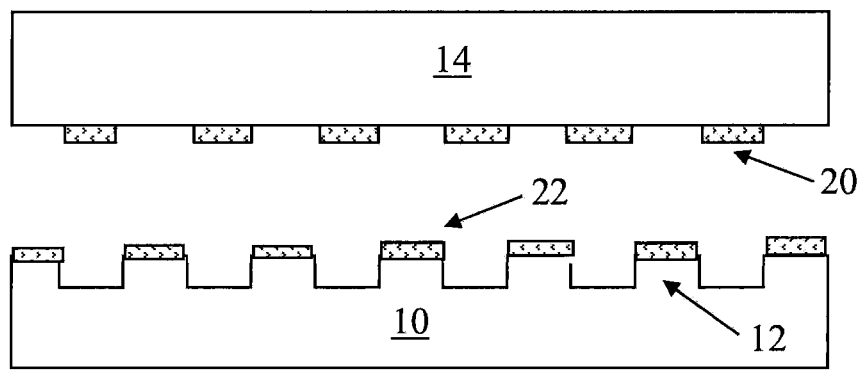
Figure 4:
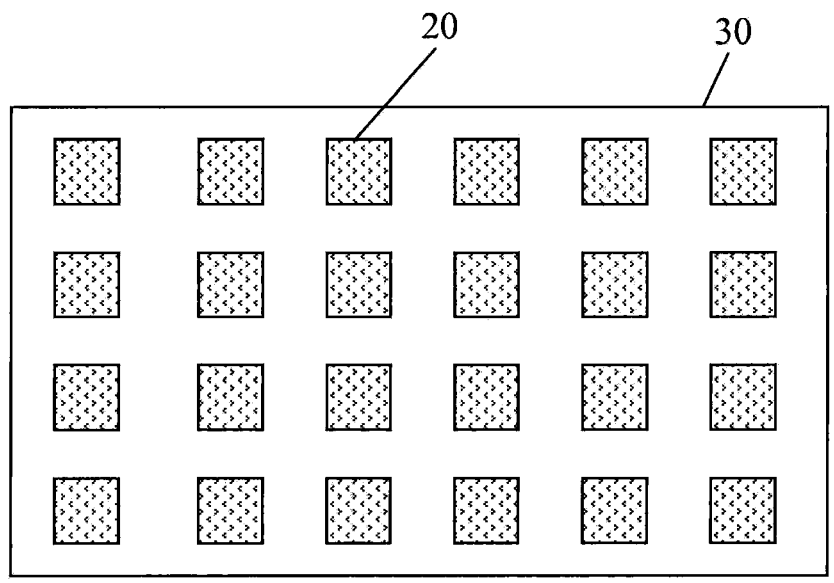

Subsequent to applying the receptor material 16 to the face of the stamp 14, the template 10 comprising the array of structures 12 can be contacted with the face of the stamp 14, as shown in FIG. 2. A slight pressure can be applied to the back of the stamp 14, as indicated by arrow 18, to bring the receptor material 16 into intimate contact with the structures 12. As a result, an array of receptors 20 remain on the face of the stamp 14 while a subtracted portion of receptor material 22 becomes deposited upon the upper surfaces of structures 12, as shown in FIG. 3. Next, the stamp 14 can be applied to a target substrate 30 to transfer the array of receptors 20 to the target substrate 30. The target substrate 30 can be, for example, a glass slide, a silicon wafer covered with native silicon dioxide (oxide) or a thicker layer of oxide, or a portion of such a wafer. The target substrate can have a negative surface charge density. The final array is depicted in FIG. 4.

Since the foregoing method employs a featureless elastomer in conjunction with subtractive contact printing to transfer the receptor material to a target substrate, the pitch and feature size of the array of receptors are not affected by the mechanical properties of the elastomer. As such, an average lateral dimension of the protein receptors can be reduced to less than 1,000 nanometers (nm, "nanoscale" size), and the pitch of the protein receptors can be reduced to less than 10 micrometers (μm).

In order to separate and screen certain viruses from a library of viruses, the substrate 30 can be placed in a solution comprising the viruses and incubated for a time sufficient to allow certain viruses to bind to the array of receptors 20. The viruses can be, for example, bateriophages such as M13 bateriophages (phages). Little or no viruses become disposed on the substrate 30 outside of the receptor areas. As a result of this binding of a portion of the viruses to the array of receptors 20, an array of viruses is formed upon the substrate 30. The surface-bound viruses can be recovered using an elution method or a microfluidic probe to capture those viruses transferred to the array of receptors 20. A microfluidic probe is a micro fluidic device composed of a chip having two apertures. The chip is placed proximal to a surface of interest and a thin film of liquid separates the chip from the surface. By injecting a liquid in the gap separating the chip from the surface using one aperture and aspirating the injected liquid using a second, nearby aperture, the injected liquid is confined on the surface of interest. The design and mode of operation of a micro fluidic probe is described in detail in Juncker et al., *Nature Materials*, vol. 4, p. 628 (2005), which is incorporated by reference herein. A microfluidic probe can be used to deliver an elution liquid, a liquid comprising a protein receptor, a liquid comprising a ligand capable of attaching to the viruses, or a combination comprising at least one of the foregoing liquids to the substrate.

In one embodiment, viruses, which are bound to transferred protein receptors, can be stained all in parallel using a fluorescently labeled receptor capable of binding to a protein coating (pVIII for M13 phages) on the transferred viruses. Detection of fluorescence signals from the substrate using a fluorescence microscope reveals where viruses have been successfully bound by protein receptors. The microfluidic probe can then be used locally to elute the virus for subsequent amplification and analysis. Alternatively, the microfluidic probe can locally deliver a liquid comprising a fluorescently labeled receptor to the substrate such as an antibody. In this case, the microfluidic probe can be both used to stain viruses on the surface of substrate and to elute the viruses.

The complexity of biological systems creates large interdependencies on pH, ionic valency and strength, and concentration, which can greatly complicate the driving forces governing their immobilization on surfaces. M13 phage solutions can undergo radical physical transformations under minor solution variations due to their filamentous structure (880 nm×6 nm) and large negative surface charge density (SCD, $\sigma$) of the virus ($\sigma_{M13}$=1 e$^{-1}$/256 A$^2$, whereas $\sigma_{DNA}$=1 e$^-$/106 A$^2$). The solution conditions for the binding of M13 phage to antibody patterns having macroscopic features (2 μm×2 μm) can be optimized to decouple these effects from studying the impact of feature size. The surface charge density of the M13 phage is a function of pH, and is maximal for values of 7 and higher. Maintaining a large negative SCD during phage binding can minimize multiple-site occupancy and non-specific background binding by increasing phage-phage and phage-silicon electrostatic repulsion, as silicon also has a negative SCD under these conditions (1 e$^-$/2381 A$^2$). Reduction of the ionic strength of buffered phage solutions by fifty percent can be used to minimize charge screening effects. Optimization of binding conditions can result in complete coverage of the patterned antibody with minimal non-specific background binding to the substrate. No surface passivation is needed when a repulsive electrostatic interaction exists between the phage and the substrate.

Figure 5:
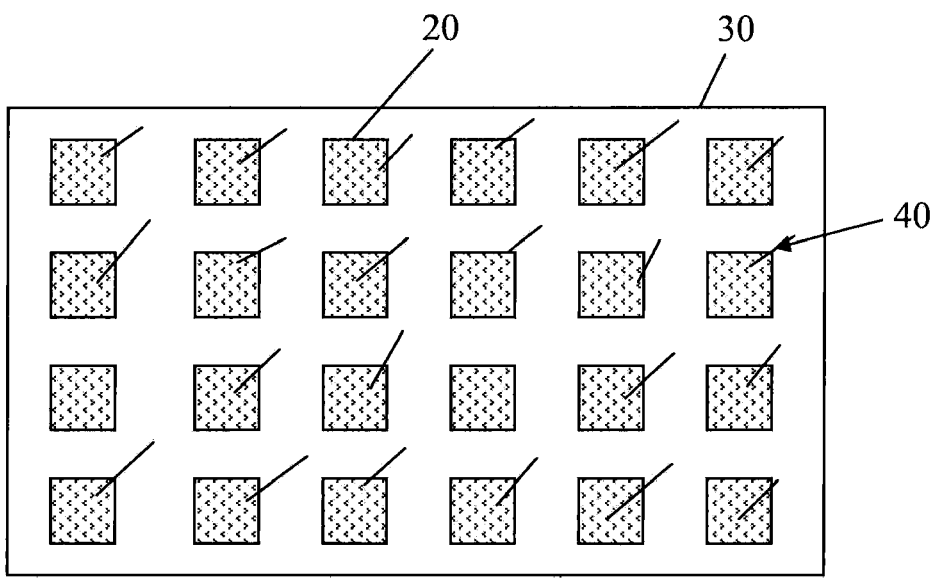

It has been unexpectedly discovered that single element arrays can be formed in which a majority of the receptor sites 20 is occupied by a single phage 40, as illustrated in FIG. 5. In particular, single element arrays can be achieved by controlling both antibody feature size and binding kinetics. Although reducing the phage solution concentration can be used to statistically achieve single element site occupancy, this reduction is limited by the binding affinity of the capture antibody. A phage solution having a phage concentration of about 10$^7$ to about 10$^9$ plaque forming units/milliliter (pfu/mL) can be used to produce individual, well-separated phage with an increase in site occupancy and pattern coverage. For concentrations above 10$^9$ pfu/mL, dramatic changes in the binding statistics suggest large local inhomogeneities in the phage solution. At very high concentrations in the range of 10$^{10}$ to 10$^{11}$ pfu/mL, changes in the physical interactions result in phage bundling and the creation of star-like patterns.

Figure 6:
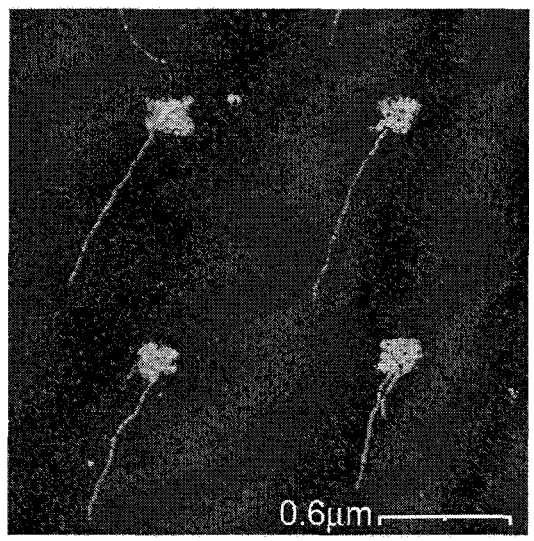
FIG. 6 illustrates an Atomic Force Microscopy (AFM) image of a phage array created using a method described herein.

Understanding the interaction between the bacteriophage protein coat and patterned antibody can help achieve single site occupancy. On 2 μm×2 μm macroscopic patterns, two bacteriophage binding conformations are present in which either complete immobilization of the protein coat or localization to the feature edge occurs. Unexpectedly, it has also been discovered that decreasing the average lateral dimension (or feature size) of the antibody receptors below about 625 nm promotes a predominantly edge-binding regime, based on the physical size and persistence length of the M13 phage (the commonly reported value is 2.2 μm, with recent reports suggesting a shorter length of 1.2 μm). That is, the binding seems to occur primarily at the edges of receptor sites. Without intending to be limited by theory, it is believed that the extension of the phage off of the antibody feature increases the repulsive electrostatic phage-silicon interaction, driving the majority of the protein coat into solution. When antibody patterns having average lateral dimensions of 240 nm×240 nm are incubated with a phage solution of 10$^9$ pfu/mL, a majority of the antibody sites become occupied with two or more phages. Reduction of the average lateral dimensions of the antibody patterns to 200 nm×200 nm can achieve arrays with a majority of sites occupied by a single phage, high coverage, and a greater degree of reproducibility. However, a number of sites remain that have two or more phages. Further reduction of the antibody feature size to 90 nm×90 nm can achieve complete single site occupancy at the cost of low coverage. Therefore, the average lateral dimension of the antibody sites patterned on the substrate desirably range from about 60 nm to about 250 nm, more specifically from about 120 nm to about 200 nm, or even more specifically from about 140 nm to about 180 nm. Also, an average pitch between the antibody sites is about 5 μm to about 700 nm, more specifically from about 2 μm to about 600 nm, or even more specifically from about 1.5 μm to about 500 nm. FIG. 6 illustrates an AFM image of a phage array created over a 200 nm wide antibody sites using the method described herein.

It is understood that while these concentrations, pitches, and dimensions are good for single phage display arrays, they can be adjusted for other applications. For example, a larger pitch can be used, causing a decrease in the required phage concentration.

The high aspect ratio of the M13 phage provides a sufficiently large hydrodynamic coefficient of drag for alignment in fluid flow. Given that the majority of the phage coat is in solution for nanoscale features, fluid flow can be used to control the direction of the phage array. By way of example, a four-fold increase in phage density can be achieved by decreasing the inter-feature pitch from 2.5 μm to 1.0 μm. Extensive bending of the phage in the fluid flow implies a strong antibody-protein binding while suggesting a possible means of studying the persistence length of filamentous systems. Phage arrays aligned in this manner can be used as templates for the fabrication of structures such as nanowires. Increasing the phage density and alignment to prefabricated structures for the creation of more complex architectures can therefore be realized using the combination of subtractive printing and flow alignment.

Organization of biological systems into functional, addressable arrays has many technological applications including micro-array technology and bottom-up nano-assemblies. Beyond the technical implications, addressable arrays of individual biological components have the potential to elucidate the intricate relationships between spatial organization and resulting functionality of external stimuli in cellular systems. Macroscopic activities such as proliferation, migration, and differentiation rely on interactions with elements whose size and organization is defined at the nanoscale.

The disclosure is further illustrated by the following non-limiting examples.

EXAMPLES

Preparation of Nanotemplates

High-resolution nanotemplates were produced using electron-beam lithography. Poly(methyl methacrylate) (PMMA) resist coated silicon wafers were exposed using an e-line electron-beam lithography system manufactured by Raith GmbH of Dortmund, Germany (voltage: 20 kilovolts (kV), aperture: 10 μm, beam current: 29 picoamperes (pA)). The PMMA resist was developed in a solution of methyl isobutyl ketone (MIBK):isopropanol at a 1:3 ratio for 30 seconds (s), immersed in isopropanol for 1 minute (min), and blown dry under a stream of N$_2$. The PMMA pattern was transferred into the silicon substrate by etching for a duration of 25 s using a low-etch-rate reactive ion etcher (manufactured by Alcatel Vacuum Technology France of Annecy, France) in a balanced process that employs sulfur hexafluoride ($SF_6$) as a precursor for the etching and octafluorocyclobutane ($C_4F_8$) for passivation of the sidewalls (Alcatel Vacuum Technology France, Annecy, France).

Protein Inking of Planar Elastomers

Sylgard® 184 polydimethylsiloxane (PDMS) elastomers, commercially available from Dow Corning of Midland, Mich., were cured at 60° C. for at least 24 hours in Petri dishes. The side of each elastomer in contact with the Petri dish was inked with about 100 microliters (μL) of antibody solution for 45 min. Anti-fd Bacteriophage (B7786 sold by Sigma of St. Louis, Mo.) was used at a concentration of 0.1 milligrams/milliliter (mg/mL) in phosphate buffered saline (PBS) (A7906 sold by Sigma). After inking, the elastomers were rinsed using PBS and deionized water and blown dry under a stream of $N_2$ for approximately 30 s.

Subtraction and Printing of Proteins

Details of the subtractive printing technique have been previously published in, e.g., Coyer, S. R., Garcia, A. J. & Delamarche, "E. Facile preparation of complex protein architectures with sub-100 nm resolution on surfaces", *Angew. Chem. Int. Ed.* vol. 46, p. 1-5 (2007), which is incorporated by reference herein. Briefly, the silicon substrates and nanotemplates were cleaned by treatment with oxygen plasma at 200 Watts for 60 s using a device manufactured by Technics Plasma 100-E of Florence, Ky. Proteins on homogenously inked elastomers were removed in selected areas by bringing the elastomers into contact with the nanotemplate for 15 s followed by release by hand. The protein patterns were transferred from the elastomers to the final substrates using a 30-s-long printing step. Intimate contact between the elastomer and the nanotemplate/substrate occurred after placing the elastomer on the nanotemplate/substrate by hand and applying a slight pressure with tweezers. Nanotemplates were cleaned of organic material by repeating the treatment with oxygen plasma before reusing.

Visualization

Atomic force microscopy (AFM) images were obtained using a Nanoscope Dimension 3000 (sold by Digital Instruments of Santa Barbara, Calif.) operated in tapping mode using 174-191 kiloHertz (kHz) silicon cantilevers sold by Nanosensors of Neuchatel, Switzerland. AFM images were planarized, displayed, and analyzed using NanoScope 6.12r1 software.

Phage Preparation

M13 bacteriophage stock (NEB) was amplified in the host bacteria *E. coli* (ER2738 NEB) using a standard phage method described in Barbas, C. F., Burton, D. R., Scott, J. K., *Phage Display: A Laboratory Manual*. Cold Spring Harbor Laboratory Press, Cold Spring Harbor, N.Y., 2001, which is incorporated by reference herein. Briefly, phage stock ($1\times10^{12}$ pfu/mL) was added to a 1:100 dilution of an overnight culture of bacteria and incubated with shaking at 37° C. for 5.5 hours. Phages were separated from bacteria via centrifugation and concentrated by polyethylene glycol/sodium chloride precipitation overnight at 4° C., followed by centrifugation. Dialysis of the resulting phage was used to remove excess salts and assure proper pH.

Sample Preparation 5 mL of phage stock in a solution of tris-buffered saline (TBS) and 0.1 weight % Tween-20 (sold by Sigma Aldrich) was incubated with the subtractive printed substrates for 1 hour, followed by gentle but thorough washing using TBST (TBS+Tween-20), TBS, and water (having an electrical resistance of 18.2 MegaOhms) and drying with compressed nitrogen. The samples were placed in a vacuum dessicator overnight prior to AFM analysis.

As used herein, the terms "a" and "an" do not denote a limitation of quantity but rather denote the presence of at least one of the referenced items. Moreover, ranges directed to the same component or property are inclusive of the endpoints given for those ranges (e.g., "about 5 wt % to about 20 wt %," is inclusive of the endpoints and all intermediate values of the range of about 5 wt % to about 20 wt %). Reference throughout the specification to "one embodiment", "another embodiment", "an embodiment", and so forth means that a particular element (e.g., feature, structure, and/or characteristic) described in connection with the embodiment is included in at least one embodiment described herein, and might or might not be present in other embodiments. In addition, it is to be understood that the described elements may be combined in any suitable manner in the various embodiments. Unless defined otherwise, technical and scientific terms used herein have the same meaning as is commonly understood by one of skill in the art to which this invention belongs.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

The invention claimed is:

1. A method for forming an array of receptors for M13 bacteriophages, comprising:

patterning an array of structures on a first substrate to form a template on a surface of the first substrate;

applying a receptor material to a face of a second substrate, wherein the second substrate comprises a featureless elastomer having a planar surface, and wherein the receptor material comprises an antibody;

contacting the face of the second substrate with the template to remove a portion of the receptor material from the second substrate, thereby forming an array of receptor material on the second substrate;

contacting a target substrate with the array of the receptor material to transfer the array of the receptor material to the target substrate; and contacting the target substrate with a solution having a pH of 7 or higher comprising the M13 bacteriophages having a concentration of about 107 to about 109 plaque forming units/milliliter (pfu/mL), and transferring a portion of the M13 bacteriophages to the array of the receptor material, wherein the target substrate has a negative surface charge density and wherein the array of the receptor material has an average lateral dimension of the structures patterned on the substrate is about 60 nanometers to about 250 nanometers and wherein the average pitch between structures is about 5 micrometers to about 700 nanometers such that a majority of sites in the array of the receptor material are occupied by a single M13 bacteriophage whereby the majority of sites is at a 1:1 ratio of the single M13 bacteriophage to a selected one of the array of the receptor material, and wherein binding of the single M13 bacteriophage to the selected one occurs predominantly at an edge of the receptor material.

2. The method of claim 1, wherein the elastomer comprises polydimethylsiloxane.

3. The method of claim 1, further comprising manipulating, recovering, or staining the M13 bacteriophages transferred to the array of the receptor material using a microfluidic probe.

4. The method of claim 3, wherein the microfluidic probe delivers an elution liquid, a liquid comprising another protein receptor, a liquid comprising a ligand capable of attaching to the M13 bacteriophages transferred to the array of the receptor material, or a combination comprising at least one of the foregoing liquids to the substrate.

5. The method of claim 4, wherein the microfluidic probe delivers a liquid comprising a fluorescently-labeled receptor to the substrate.

6. The method of claim 5, wherein the microorganisms transferred to the array of the receptor material are detected using immunofluorescent staining.

7. The method of claim 6, wherein the microfluidic probe delivers a liquid to the target substrate that comprises a fluorescently-labeled antibody capable of binding to a protein coating on the M13 bacteriophages transferred to the array of the receptor material.

8. The method of claim 1, further comprising recovering the M13 bacteriophages transferred to the array of the receptor material using elution.

9. The method of claim 1, wherein said method arranges the transferred portion of the M13 bacteriophages in a M13 bacteriophage array, and wherein the direction of the M13 bacteriophage array is controlled using fluid flow.

10. The method of claim 1, wherein average lateral dimensions of the structures patterned on the substrate are less than or equal to about 200 nm×200 nm.

11. The method of claim 1, wherein the target substrate is a glass slide, a silicon wafer coated with a native silicon dioxide or a thicker silicon dioxide layer, or a portion of said coated silicon wafer.

* * * * *